United States Patent [19]

Summers, Jr.

[11] Patent Number: 4,897,422

[45] Date of Patent: Jan. 30, 1990

[54] LIPOXYGENASE INHIBITING COMPOUNDS

[75] Inventor: James B. Summers, Jr., Libertyville, Ill.

[73] Assignee: Abbott Laboratories, Abbott Park, Ill.

[21] Appl. No.: 12,978

[22] Filed: Feb. 10, 1987

[51] Int. Cl.[4] .................... C07C 83/10; A61K 31/185; A61K 31/085; A61K 31/13
[52] U.S. Cl. ..................... 514/575; 514/555; 562/621; 562/623; 562/874; 260/545 R
[58] Field of Search ...... 260/500.5 H, 501.1, 260/545 R; 514/575, 555, 576; 562/623

[56] References Cited

U.S. PATENT DOCUMENTS

| | | | |
|---|---|---|---|
| 3,855,242 | 12/1984 | Chapman et al. | 260/330.5 |
| 3,890,377 | 6/1975 | Marshall | 260/500.5 H |
| 3,928,384 | 12/1975 | Descamps et al. | 260/330.5 |
| 4,604,407 | 8/1986 | Haslanger et al. | 514/575 |
| 4,738,986 | 4/1988 | Kneen et al. | 260/500.5 H |

FOREIGN PATENT DOCUMENTS 0196184  3/1986  European Pat. Off. .
2068420 10/1969  France .

*Primary Examiner*—J. E. Evans
*Attorney, Agent, or Firm*—Robert W. Stevenson; Steven F. Weinstock; Steven R. Crowley

[57] ABSTRACT

Compounds of the formula:

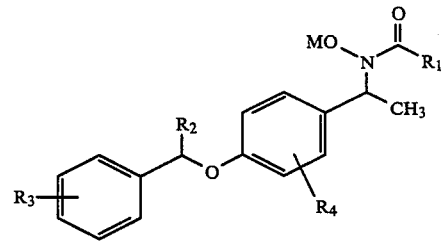

where $R_1$ is amino or methyl; $R_2$ is $C_1$–$C_2$ alkyl; $R_3$ is one or more substituents selected from hydrogen, halogen or trihalomethyl; $R_4$ is one or more substituents selected from hydrogen, halogen, trihalomethyl, $C_1$ to $C_4$ alkoxy or $C_1$ to $C_4$ alkyl; and M is hydrogen, a pharmaceutically acceptable cation, aroyl, or $C_1$ to $C_6$ alkoyl are inhibitors of 5- and/or 12-lipoxygenase enzymes.

6 Claims, No Drawings

LIPOXYGENASE INHIBITING COMPOUNDS

BACKGROUND OF THE INVENTION

This invention relates to organic compounds which inhibit lipoxygenase enzymes. It also relates to methods of inhibiting lipoxygenase enzymes in human and animal hosts in need of such treatment.

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs).

Similarly 12- and 15-lipoxygenase, convert arachidonic acid to 12- and 15-HPETE respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs $C_4$ and $D_4$ are potent constrictors of human airways in vitro, and aerosol administration of these substances to non-asthmatic volunteers induces broncho-constriction. $LTB_4$ and 5-HETE are potent chemotactic factors for imflammatory cells such as polymorphonuclear leukocytes. They also have been found in the synovial fluid of rheomatoid arthritic patients. Leukotrienes have also been implicated as important mediators in allergic rhinitis psoriasis, adult respiratory distress syndrome, Crohn's disease, endotoxin shock, and ischemia induced myocardial injury among others. The biological activity of the LTs has been reviewed by Lewis and Austen (*J. Clinical Invest.* 73,89, 1984 and by J. Sirois (*Adv. Lipid Res.* 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes are believed to play an important role in the biosynthesis of mediators of asthma, allergy arthritis, psoriasis, and inflammation. Blocking these enzymes interrupts the biochemical pathways believed to be involved in these disease states.

One of the problems associated with the development of lipoxygenase inhibitors is that many such compounds are poorly absorbed into the blood stream if administered orally. Thus, it is difficult to achieve high plasma levels. Another deficiency of many inhibitors is that even when they are absorbed, they are subject to metabolism and do not have long plasma duration. Metabolism cleaves the compounds into metabolites which are believed to have little lipoxygenase enzyme inhibition. Thus, there is a need for lipoxygenase inhibiting compounds with high plasma levels and long duration, particularly because lipoxygenase enzymes are belived to be implicated in a variety of disease states.

DETAILED DESCRIPTION OF THE INVENTION

The lipoxygenase enzyme inhibiting compounds of the present invention have extended half lives, are absorbed well, and achieve unexpected plasma levels. These compounds include compounds of formula I:

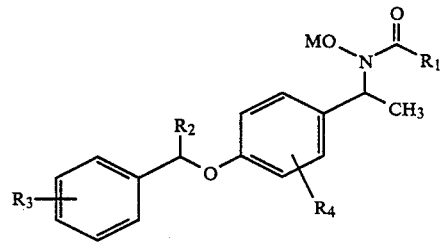

where $R_1$ is amino or methyl, and $R_2$ is a $C_1$–$C_2$ alkyl. $R_3$ is one or more substituents selected from hydrogen, halogen or trihalomethyl. $R_4$ represents one or more substituents selected from hydrogen, halogen, trihalomethyl, $C_1$ to $C_4$ alkoxy or $C_1$ to $C_4$ alkyl. Finally, M is hydrogen, a pharmaceutically acceptable cation, aroyl, or $C_1$ to $C_6$ alkoyl.

The present invention further includes a method of inhibiting 5- and/or 12-lipoxygenase activity in a mammal in need of such treatment by administering to such mammal compounds of the present invention as described above in an amount effective to inhibit such activity.

Disease states which may be treated in humans or lower animal hosts by the methods described above include, but are not limited to, asthma rheumatoid arthritis, gout, psoriasis, allergic rhinitis, adult respiratory distress syndrome, Crohn's disease, endotoxin shock, and/or ischemia induced-myocardial injury.

Examples of compounds which are themselves within the scope of the present invention and/or can be used according to the methods of the present invention include the following:

N-hydroxy-(1-(4-(1-phenylethoxy)phenyl)ethyl)acetamide

N-hydroxy-(1-(4-(1-phenylethoxy)phenyl)ethyl)urea

N-hydroxy-(1-(4-(1-(4-fluorophenyl)ethoxy)phenyl)ethyl)acetamide

N-hydroxy-(1-(4-(1-(4-fluorophenyl)ethoxy)phenyl)ethyl)urea

N-hydroxy-(1-(4-(1-(4-chlorophenyl)ethoxy)phenyl)ethyl)acetamide

N-hydroxy-(1-(4-(1-(4-chlorophenyl)ethoxy)phenyl)ethyl)urea

N-hydroxy-(1-(4-(1-phenylpropyloxy)phenyl)ethyl)acetamide

N-hydroxy-(1-(4-(1-(3-trifluoromethylphenyl)ethoxy)phenyl)ethyl)acetamide

N-hydroxy-(1-(4-(1-phenylethoxy)-3-chlorophenyl)ethyl)acetamide

N-hydroxy-(1-(4-(1-phenylethoxy)-3,5-dimethoxyphenyl)ethyl)acetamide

N-hydroxy-(1-(4-(1-phenylethoxy)-3,5-dimethylphenyl)ethyl)acetamide

N-hydroxy-(1-(4-(1-phenylethoxy)-2-ethylphenyl)ethyl)acetamide

N-hydroxy-(1-(4-(1-phenylethoxy)-3-trifluoromethyl)phenylethyl)acetamide

N-hydroxy-(1-(4-(1-phenylpropyloxy)phenyl)ethyl)urea

N-hydroxy-(1-(4-(1-(4-trifluoromethylphenyl)ethoxy)phenyl)ethyl)urea

N-hydroxy-(1-(4-(1-phenylethoxy)-3-fluorophenyl)ethyl)urea

N-hydroxy-(1-(4-(1-phenylethoxy)-3,5-dimethoxyphenyl)ethyl)urea

N-hydroxy-(1-(4-(1-phenylethoxy)phenyl)ethyl-)acetamide sodium salt

N-hydroxy-(1-(4-(1-phenylethoxy)phenyl)ethyl)urea potassium salt

N-hydroxy-(1-(4-(1-phenylethoxy)phenyl)ethyl-)acetamide ammonium salt

N-hydroxy-(1-(4-(1-phenylethoxy)phenyl)ethyl-)acetamide triethyl ammonium salt

N-hydroxy-(1-(4-(1-phenylethoxy)phenyl)ethyl-)acetamide tetraethyl ammonium salt N-butyryloxy-(1-(4-(1-phenylethoxy)phenyl)ethyl-)urea N-benzoyloxy-(1-(4-(1-phenylethoxy)phenyl)ethyl-)urea The term alkyl is used herein to mean straight and branched chain radicals, including, but not limited to, methyl, ethyl, n-propyl, isopropyl, n-butyl, sec-butyl, isobutyl, tert-butyl, and the like.

The term alkoxy is used herein to mean straight and branched chained oxygen ether radicals, including, but not limited to methoxy, ethoxy, isopropoxy, n-butoxy, sec-butoxy, isobutoxy, tert-butoxy, and the like.

The term alkoyl is used herein to mean straight or branched carbonyl radicals, including, but not limited to, formyl, acetyl, propionyl, butyryl, isobutyryl, pivaloyl, and the like.

The term aroyl is used herein to mean substituted and unsubstituted aromatic ether radicals, including, but not limited to, benzoyl, 1-naphthoyl, 2-naphthoyl, and the like.

The term halo and halogen as used herein refer to radicals derived from the elements fluorine, chloride, bromine, and iodine.

The term "pharmaceutically acceptable cation" refers to non-toxic cations, including but not limited to those based on the alkali and alkaline earth metals, such as sodium lithium, potassium, magnesium, and the like, as well as nontoxic ammonium, quaternary ammonium, and amine cations, including, but not limited to, ammonium tetramethylammonium, tetrathylammonium, methylamine, dimethylamine, trimethylamine, triethylamine, ethylamine, and the like.

Method of Treatment

This invention provides a method of treatment of inhibiting 5- and/or 12-lipoxygenase activity in a human or lower animal host in need of such treatment which method comprises administration to the human or lower animal host of a compound previously described in an amount effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intraarterial injection or infusion techniques, without limitation. The term "topically" encompasses administration rectally and by inhalation spray, as well as by the more common routes of the skin and mucous membranes of the mouth and nose.

Total daily dose of the compounds of this invention administered to a host in a single or divided doses maybe in amounts, for example, of from about 0.001 to about 100 mg/Kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors, including the body weight, general health, sex, diet, time and route of administration, rates of absorption and excretion, combination with other drugs and the severity of the particular disease being treated.

Formulation of the Pharmaceutical Composition

This invention also provides for compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose, any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable non-irritating excipient such as cocoa butter and polyethylene glycols, which are solid at ordinary temperatures but liquid at body temperature and which, therefore, melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsule, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

Synthesis of the Compounds

Compounds of this invention where $R_1$ is methyl can be prepared according to the reaction sequence described in Scheme 1. Although the sequence illustrates the compound of formula I above where $R_2$ is methyl and $R_3$ and $R_4$ are hydrogen, it will be seen from the examples that other compounds of this invention can be prepared in the same manner using the appropriate starting materials.

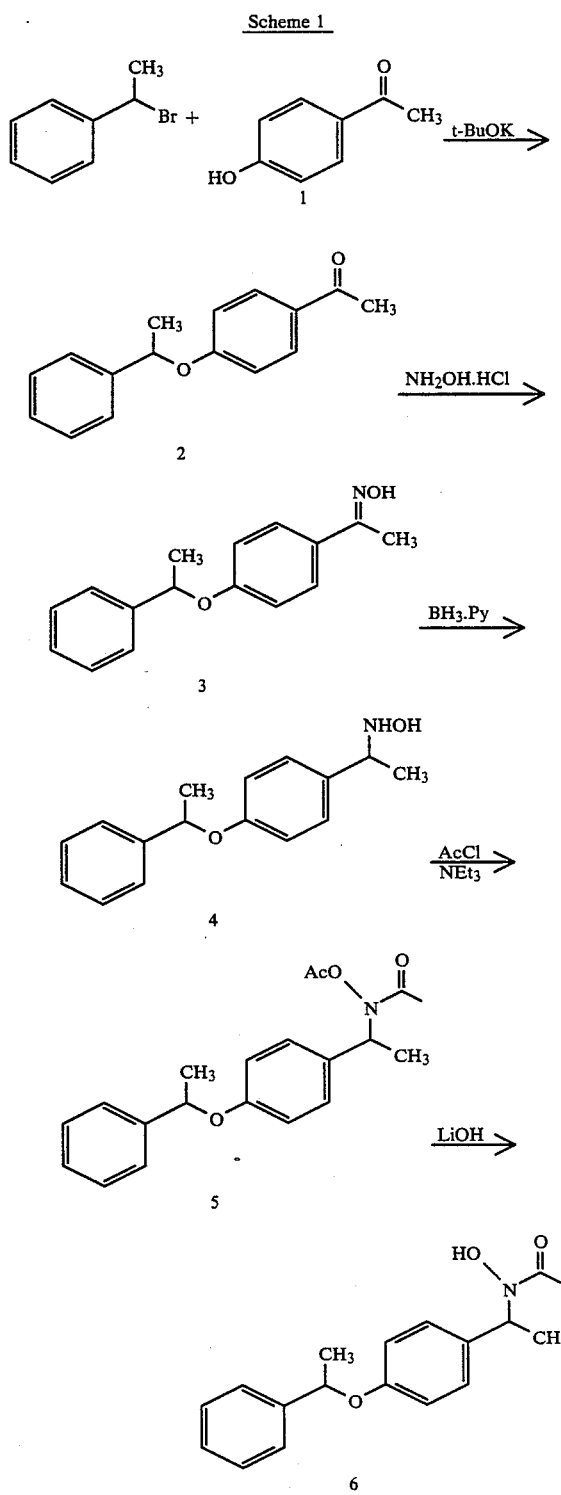

SCHEME I

4-Hydroxyacetophenone (1) is converted to 1-(4-(1-phenylethoxy)phenyl)ethyl acetophenone (2) by adding potassium t-butoxide to a solution of 4-hydroxyacetophenone (1) in dimethylsulfoxide. 1-phenylethyl-bromide is added to the mixture to produce the 1-(4-(1-phenylethoxy)phenyl)ethyl acetophenone (2). The acetophenone (2) is treated with hydroxylamine in ethanol/pyridine to produce the oxime (3). This is reduced to the hydroxylamine (4) with borane pyridine complex and then converted to the N,O-diacetate (5) with acetyl chloride and triethylamine. The diacetate is converted to the hydroxamic acid (6) by hydrolysis with lithium hydroxide. Other reagents may also be used to carry out the same transformations. For example (3) may be converted to (4) using borane dimethylamine or other borane amine complexes or with sodium cyanoborohydride. Hydroxylamine (4) can also be converted to (5) with acetic anhydride and a base such a pyridine.

Compounds of formula I where $R_1$ is $-NH_2$ can be prepared according to the method outlined in Scheme 2 below. Although the sequence illustrates the case where $R_2$ is methyl and $R_3$ and $R_4$ are both hydrogen, it will be seen from the examples that other compounds of this invention can also be prepared in this manner.

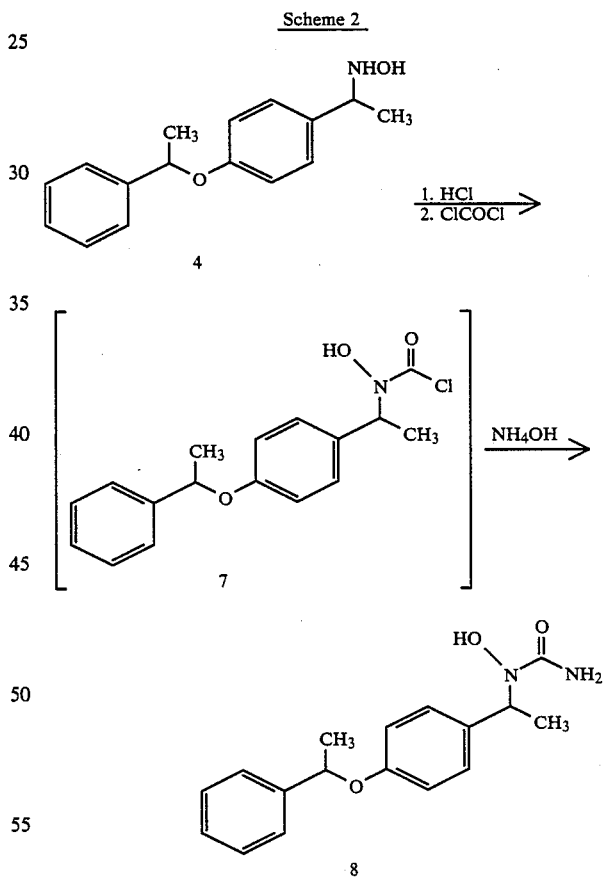

SCHEME II

The hydroxylamine (4), the synthesis of which was described above, is treated with gaseous HCl followed by phosgene. The resulting carbamoyl chloride (7) is reacted without isolation with aqueous ammonia to yield the urea (8).

Compounds of formula I wherein $R_1$ is $NH_2$ can also be prepared according to Scheme III, below. The sequence illustrates the case where $R_2$ is methyl and $R_3$ and R4 are hydrogen. However, it will be seen from the examples that other compounds of this invention can also be prepared in this manner.

Scheme 3

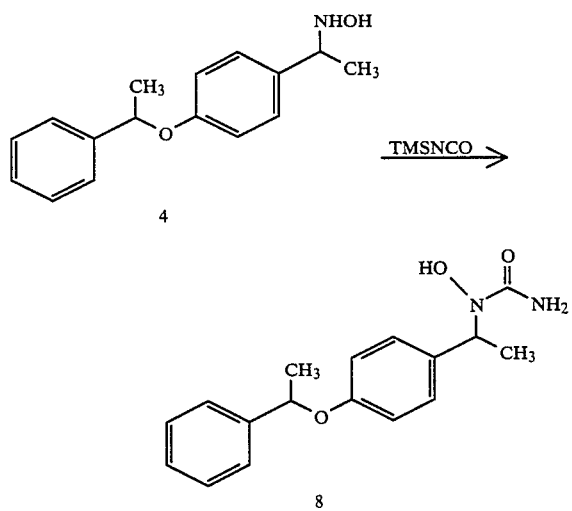

SCHEME III

Hydroxylamine (4) is treated with trimethylsilylisocyanate, followed by ammonium chloride workup to give the urea (8).

The following examples further illustrates the synthesis and use of compounds of this invention. The appropriate designations of $R_1$, $R_2$, $R_3$, and $R_4$ as defined by formula I are designated for each example.

EXAMPLE 1

N-hydroxy-N-(1-(4-(1-phenylethoxy)phenyl)ethyl)acetamide (a) 1-(4-(1-phenylethoxy)phenyl)ethyl acetophenone was prepared by adding potassium t-butoxide (2.84 gr, 25.4 mmole) to a solution of 4-hydroxyacetophenone (3.0 g, 22.1 mmole) in dimethylsulfoxide (30 ml). After 15 minutes, 1-phenylethylbromide (5.1 g, 27.6 mmole) was added and the mixture stirred for an additional 60 minutes. The reaction mixture was poured into water (100 mL) and extracted with ether. This solution was dried over the MgSO4 and evaporated. The resulting residue was carried on without further purification.

(b) 1-(4-(1-phenylethoxy)phenyl)ethyl acetophenone oxime was prepared by dissolving the 1-(4-(1-phenylethoxy)phenyl)ethyl acetophenone from Example 1(a)(4.2 g, 17.5 mmole) and hydroxylamine hydrochloride (4.2 g, 60.4 mmole) in a mixture of ethanol (30 ml) and pyridine (30 ml). The solution was heated at 50° C. for two hours. Most of the solvent was removed in vacuo, and the residue dissolved in ether. After washing with 2N HCl (50 ml), the solution was dried over MgSO4 and evaporated. A thick oil was obtained and was carried on without further purification.

(c) 1-(4-(1-phenylethoxy)phenyl)ethylhydroxylamine was prepared by dissolving the 1-(4-(1-phenylethoxy)phenyl)ethyl acetophenone oxime (4.3 g, 16.9 mmole) of Example 1(b) in ethanol (80 ml) and cooling the solution to 0° C. Borane-pyridine complex (4.5 g, 50.7 mmole) was added via syringe under nitrogen followed ten minutes later by 6N HCl (17 ml). Within thirty minutes, the reaction was complete, and the mixture was brought to pH 9 with the addition of solid sodium carbonate or 2N NaOH. The mixture was extracted into ether and dried over MgSO4. After evaporation, a yellow oil resulted which was carried on without further purification.

(d) N-acetoxy-N-(1-(4-(1-phenylethoxy)phenyl)ethyl)acetamide. The hydroxylamine (2.93 g, 11.4 mmole) prepared above and triethylamine (2.89 ml, 28.5 mmole) were dissolved in THF (30 ml) and cooled to 0° C. in an ice bath. Acetyl chloride (1.8 g, 22.8 mmole) was added slowly. After stirring for thirty minutes, the reaction mixture was washed with 2N HCl, dried with MgSO4, and evaporated. The residue was chromatographed in silica gel, eluting with 60% ether in pentane. A gummy solid (2.5 g) was obtained.

(e) N-hydroxy-N-(1-(4-(1-phenyl)ethoxyphenyl)ethylacetamide. The material obtained in the previous step (2.5 g, 7.2 mmole) was dissolved in isopropyl alcohol (15 mL) and lithium hydroxide (2.5 g) in water (15 mL). After stirring for thirty minutes, most of the solvent was removed in vacuo and the mixture was made acidic with the addition of 2N HCl. The product was extracted into ether, which was then dried over MgSO4 and evaporated. A colorless oil was obtained after chromatography with ether. ($R_1$=CH3, $R_4$=$R_3$=H, $R_2$=CH3).

NMR (300 MHz, DMSO-$d_6$): 1.38 (d, 3H); 1.52 (d, 3H); 1.94 (s, 3H); 5.48 (m, 2H); 6.83 (d, 2H); 7:14 (d, 2H); 7.20–7.45 (m, 5H); 9.45 (d, 1H).

Mass spectrum (EI): 299M+, 282,240,225,121,105.

EXAMPLE 2

N-hydroxy-N-(1-(4-(1-phenylethoxy)phenyl)ethyl)urea (a) 1-(4-(1-phenylethoxy)phenyl)ethylhydroxylamine was prepared according to the method of Example 1(c).

(b) N-hydroxy-N-(1-(4-(1-phenylethoxy)phenyl)ethyl)urea was prepared using Scheme 2 by refluxing 1-(4-(1-phenylethoxy)phenyl)ethylhydroxylamine (2.22 g 8.64 mmole) for thirty minutes with trimethylsilylisocyanate (1.19 gr, 10.4 mole) in dioxane (30 ml). The reaction mixture was then washed with saturated NH4Cl solution, dried with MgSO4, and evaporated. The residue was washed with ether to give a white solid (1.3 g).

Alternatively, the same compound can be prepared using the method of Scheme 3. The material of Example 2(a) is dissolved in toluene, and HCl gas is bubbled through the mixture at a moderate rate for about four minutes. The mixture is heated to reflux and phosgene is bubbled through at a moderate rate for about 15 minutes. After an additional one hour reflux, the mixture was allowed to cool to room temperature and then added to excess cold ammonium hydroxide solution. The precipitate was collected and recrystallized from aqueous ethanol ($R_1$=NH2, $R_2$=CH3, $R_3$=$R_4$=H).

Melting point: 125°–130° C.

NMR (300 MHz, DMSO-$d_6$): 1.53 (d, 3H); 1.82 (d, 3H); 5.19 (q, 1H); 5.95 (q, 1H), 6.23 (brs, 2H); 6.81 (m, 2H); 7.15 (m, 2H); 7.22–7.43 (m, 5H) 8.95 (brs, 1H).

Mass sprectrum (CI—NH3): 301 (M=1)+, 283,240,225,121.

EXAMPLE 3

N-hydroxy-N-(1-(4-(1-(4-fluorophenyl)ethoxy)phenyl)-ethyl)acetamide (a) 1-(4-fluorophenyl)ethanol. 4-Fluorophenylacetophenone (10 g, 72 mmole) was dissolved in methanol (100 ml) and sodium borohydride (2.74 g, 72 mmole) was added. After one hour the solvent was removed in vacuo and the residue dissolved in ether and washed with 2N HCl. The ether layer was dried with $MgSO_4$ and evaporated to give the desired product.

(b) 1-(4-Fluorophenyl)-1-chloroethane. Triphenyl phosphine (20.75 g, 79 mmole) was dissolved in $CH_2Cl_2$ and bromine (12.68 g, 79 mmole) was added. To this was added the material prepared as in part a above (10.1 g, crude). Triphenylphosphine oxide was filtered off and the solvent was removed in vacuo.

(c) 4-(1-(4-Fluorophenyl)ethoxy)acetophenone was prepared using the method of example 1 part a, except using the material prepared as in part b, above instead of 1-bromobutane.

(d) N-hydroxy-N-(1-(4-(1-(4-fluorophenyl)-ethoxy)-phenyl)ethyl)acetamide. The desired compound was prepared according to the method of example 1, parts b-e, except using the material prepared as in part c above, instead of 1-(4-(1-phenylethoxy)phenyl)-ethylacetophenone ($R_1$=CH$_3$, $R_2$=CH$_3$, $R_3$=3—F, $R_4$=H).

NMR (300 MHz, DMSO-d6): 1.36 (d, 3H); 1.51 (d, 3H); 1.98 (s, 3H); 5.50 (m, 2H); 6.82 (m, 2H); 7.15 (m, 4H); 7.45 (m, 2H); 9.48 (brs, 1H).

Mass spectrum (CI-NH$_3$): 335 (N+NH$_4$)$^+$, 318 (M=1)$^+$, 302,274,243,198.

EXAMPLE 4

N-hydroxy-N-(1-(4-(1-(4-fluorophenyl)ethoxy)phenyl)ethyl)urea (a) 1-(4-(1-(4-fluorophenyl)ethoxy)phenyl)ethyl hydroxylamine was prepared according to the method of example 1, parts and a-b, except using 4-(1-(4-fluorophenyl)ethoxy)acetophenone, prepared as described in example 3, part c.

(b) N-hydroxy-N-(1-(4-(1-(4-fluorophenyl)ethoxy)-phenyl)ethyl) urea was prepared according to the method of example 2, part b, except using the material prepared as in part a, above, instead of 1-(4-(1-phenylethoxy)phenyl)ethylydroxylamine ($R_1$=NH$_2$, $R_2$=CH$_3$, $R_3$=3-F, $R_4$=H.

NMR (300 MHz, DMSOd$_6$): 1.32: (d. 3H); 1.53 (d. 3H); 5.49 (m, 2H); 6.23 (s, 2H); 6.82 (M, 2H); 7.17 (m, 4H); 7.45 (m, 2H); 8.97 (brs, 1H).

Mass Spectrum (EI): 318 M$^+$, 301,243.

EXAMPLE 5

N-hydroxy-N-(1-(4-(1-(4-chlorophenyl)ethoxy)-phenyl)-ethyl)acetamide

The desired compound was prepared according to the method of example 3, except using 4-chloroacetophenone instead of 4-fluoroacetophenone ($R_1$=CH$_3$, $R_2$=CH$_3$, $R_3$=3-Cl, $R_4$=H).

NMR (300 MHz, DMSO-d$_6$): 1.36 (d, 3H); 1.52 (d, 3H); 1.96 (s, 3H); 5.50 (m, 2H); 6.83 (d, 2H); 7.14 (d, 2H); 7.42 (m, 4H); 9.46 (brs, 1H).

Mass Spectrum (Cl); 334,316,259,139,121.

EXAMPLE 6

4-hydroxy-N-(1-(4-(1-(4-chlorophenyl)ethoxy)phenyl)ethyl)urea

The desired compound was prepared according to the method of example 4, except using 4-chloroacetophenone instead of 4-fluorophenylacetophenone ($R_1$=NH$_2$, $R_2$=CH$_3$, $R_3$=3-Cl, $R_4$=H).

NMR (300 MHz, CDCL$_3$): 1.47 (d, 3H); 1.60 (d, 3H); 5.14 (brs, 2H); 5.26 (q, 1H): 5.38 (q,, 1H); 6.20 (brd, 1H); 6.79 (d, 2H); 7.24 (d, 2H); 7.30 (m, 4H).

Mass Spectrum (EI): No M$^+$, 317,259,139,121,103.

Examples 7–13 can be prepared by methods generally analogous to those described in example 1.

EXAMPLE 7

N-hydroxy-(1-(4-(1-phenylpropyloxy)phenyl)ethyl)acetamide $R_1$=CH$_3$ $R_2$=C$_2$H$_5$, $R_3$=H, $R_4$=H

EXAMPLE 8

N-hydroxy-(1-(4-(1-(3-trifluoromethylphenyl)ethoxy)-phenyl)ethyl)acetamide $R_1$=CH$_3$, $R_2$=CH$_3$, $R_3$=3-CF$_3$, $R_4$=H

EXAMPLE 9

N-hydroxy-(1-(4-(1-phenylethoxy)-3-chlorophenyl)ethyl)acetamide $R_1$=CH$_3$, $R_2$=CH$_3$, $R_3$=H, $R_4$=3-Cl

EXAMPLE 10

N-hydroxy-(1-(4-(1-phenylethoxy)-3,5-dimethoxyphenyl ethyl)acetamide $R_1$=CH$_3$, $R_2$=CH$_3$, $R_3$=H, $R_4$=3,5-(CH$_3$O)$_2$

EXAMPLE 11

N-hydroxy-(1-(4-(1-phenylethoxy)-3,5-dimethylphenyl ethyl)acetamide $R_1$=CH$_3$, $R_2$=CH$_3$, $R_3$=H, $R_4$=3,5-(CH$_3$)$_2$

EXAMPLE 12

N-hydroxy-(1-(4-(1-phenylethoxy)-2-ethylphenyl)ethyl)acetamide $R_1$=CH$_3$, $R_2$=CH$_3$, $R_3$=H, $R_4$=2-C$_2$H$_5$

EXAMPLE 13

N-hydroxy-(1-(4-(1-phenylethoxy)-3-trifluoromethylphenyl)ethyl)acetamide $R_1$=CH$_3$, $R_2$=CH$_3$, $R_3$=H, $R_4$=CF$_3$ Examples 14–17 can be prepared by methods generally analogous to those described in example 12.

EXAMPLE 14

N-hydroxy-(1-(4-(1-phenylpropyloxy)phenyl)ethyl)urea $R_1$=NH$_2$, $R_2$=C$_2$H$_5$, $R_3$=H, $R_4$=H

EXAMPLE 15

N-hydroxy-(1-(4-(1-(4-trifluoromethylphenyl)ethoxy)-phenyl)ethyl)urea $R_1$=NH$_2$, $R_2$=CH$_3$, $R_3$=4-CF$_3$, $R_4$=H

EXAMPLE 16

N-hydroxy-(1-(4-(1-phenylethoxy)-3-fluorophenyl)ethyl)urea $R_1$=NH$_2$, $R_2$=CH$_3$, $R_3$=H, $R_4$=3-F

EXAMPLE 17

N-hydroxy-(1-(4-(1-phenylethoxy)-3,5-dimethoxyphenyl)ethyl)urea $R_1$=NH$_2$, $R_2$=CH$_3$, $R_3$=H, $R_4$=3,5-(CH$_3$O)$_2$

EXAMPLE 18

N-hydroxy-(1-(4-1-phenylethoxy)phenyl)ethyl)acetamide sodium salt

The material prepared as in example 1 is dissolved in tetrahydrofuran and one equivalent of sodium hydride is added. After hydrogen evolution ceases, the solvent is removed in vacuo to yield the desired product. $R_1$=CH$_3$, $R_2$=CH$_3$, $R_3$=H, $R_4$=H, M=Na.

EXAMPLE 19

N-hydroxy-(1-(4-1-phenylethoxy)phenyl)ethyl)urea potassium

The material prepared as in example 2 is dissolved in tetrahydrofuran and one equivalent of potassium hydride is added. After hydrogen evolution ceases, the solvent is removed in vacuo to yield the desired product. $R_1$=NH$_2$, $R_2$=CH$_3$, $R_3$=H, $R_4$=H, M=K.

EXAMPLE 20

N-hydroxy-(1-(4-(1-phenylethoxy)phenyl)ethyl)acetamide ammonium salt

The material prepared as in example 1 is dissolved in tetrahydrofuran and ammonia is bubbled through. The solvent is removed in vacuo to yield the desired product. $R_1$=CH$_3$, $R_2$=CH$_3$, $R_3$=H, $R_4$=H, M=NH$_4$.

EXAMPLE 21

N-hydroxy-(1-(4-(1-phenylethoxy)phenyl) acetamide triethyl ammonium salt

The material prepared as in example 1 is dissolved in tetrahydrofuran and one equivalent of triethylamine is added. The solvent is removed in vacuo to yield the desired product. $R_1$=CH$_3$, $R_2$=CH$_3$, $R_3$=H, $R_4$=H, M=NH(C$_2$H$_5$)$_3$.

EXAMPLE 22

N-hydroxy-(1-(4-(1-phenylethoxy)phenyl)ethyl)Acetamide tetraethyl ammonium salt

The material prepared as in example 1 is dissolved in tetrahydrofuran and one equivalent of tetraethylammonium hydroxide is added. The solvent is removed in vacuo to yield the desired product. $R_1$=CH$_3$, $R_2$=CH$_3$, $R_3$=H, $R_4$=H, M=N(C$_2$H$_5$)$_4$.

EXAMPLE 23

N-butyryloxy-(1-(4-(1-phenylethoxy)phenyl)ethyl)urea

The material prepared as in example 2 and 1.1 equivalent of triethylamine are dissolved in tetrahydrofuran and 1 equivalent of butryryl chloride is added. Ether is added and the material is washed with 2N HCl, dried with MgSO$_4$ and then evaporated in vacuo to yield the desired product. $R_1$=NH$_2$, $R_2$=CH$_3$, $R_3$=H, $R_4$=H, M=COC$_3$H$_7$.

EXAMPLE 24

N-benzoyloxy-(1-(4-(1-phenylethoxy)phenyl)ethyl)urea

The material prepared as in example 2 and 1.1 equivalent of triethylamine are dissolved in tetrahydrofuran and 1 equivalent of benzoyl chloride is added. Ether is added and the material is washed with 2N HCl, dried with MgSO$_4$ and then evaporated in vacuo to yield the desired product. $R_1$=NH$_2$, $R_2$=CH$_3$, $R_3$=H, $R_4$=H, M=COC$_6$H$_5$.

Lipoxygenase IC$_{50}$ Determination

Assays to determine 5-lipoxygenase activity were performed in 200 ml incubations containing the 20,000xg supernatant from 1.5 million homogenized RBL-1 cells and various concentratins of the test compound. Reactions were initiated by addition of radiolabeled arachidonic acid and terminated by acidification and ether extraction. Reaction products were separated from nonconverted substrate by thin layer chromatography and measured by liquid scintillation spectroscopy. All incubations are performed in triplicate. Inhibition of 5-lipoxygenase activity was calculated as the ratio of the amount of product formed in the presence and absence of inhibitor. IC$_{50}$ values and 95% confidence limits were computed from linear regression analysis of percentage inhibition versus log concentration plots. Results for compounds of the foregoing examples are indicated in Table 1. Inhibition in this assay is believed to be a necessary requisite for lipoxygenase inhibition in vivo.

TABLE 1

In Vitro Inhibitory Potencies of Compounds of this Invention Against 5-Lipoxygenase from RBL-1 20,000 xg Supernatant

| Example | $R_1$ | $R_2$ | $R_3$ | $R_4$ | I C$_{50}$(uM) |
|---|---|---|---|---|---|
| 1 | CH$_3$ | CH$_3$ | H | H | 0.50 |
| 2 | NH$_2$ | CH$_3$ | H | H | 0.62 |
| 3 | CH$_3$ | CH$_3$ | F | H | 0.52 |
| 5 | CH$_3$ | CH$_3$ | Cl | H | 0.55 |
| 6 | NH$_2$ | CH$_3$ | Cl | H | 0.24 |

Rat Peritoneal Analphyaxis Model

The ability of compounds to inhibit leukotriene synthesis in vivo were assessed in a rat peritoneal analphylaxia model similar to that described by Orange et al., J. Exper. Med. 127, 767, 1968. Groups of rats are injected intraperitoneally with rabbit antibody to bovine serum albumin (BSA) followed 3 hours later by an i.p. injection of BSA. This triggers the synthesis of leukotrienes in the peritoneal cavity. The rats are sacrificed 15 minutes after this challenge the peritoneal fluids collected, and processed. The amount of leukotrienes are determined routinely by radioimmunoassay, in units of LTC equivalents. To evaluate oral effectiveness selected inhibitors are administered by gavage 1 hour prior to antigen challenge. Results of compounds of this invention in this assay are described in Table II.

Determination of Plasma Levels

Rats were dosed orally with solution or suspensions of compounds by gavage. At selected time points after dosing blood was removed from the tail vein and the plasma proteins were precipitated with 2 volumes of methanol. After centrifugation the supernatant was injected unto a C$_{18}$ adsorbosphere HPLC column and eluted with a mobile phase of triethylamine and acetonitrile containing acetohydroxamic acid. The amount of drug present in the plasma was determined by comparison of peak integrations to reference standards dissolved in plasma. Similar procedures were used for dogs, monkeys, and mice. Results of compounds of this invention in this assay are described in Table II.

Determination of Duration (Plasma Half Life)

Rats were injected intravenously with compounds through a jugular cannula. At various time points after injection blood samples were collected from the tail vein and processed as described above under "Determination of Plasma Levels". Half lives were calculated from a linear regression analysis of time points after the distribution phase. Similar methods were used for dog, monkey and mice. Results of compounds of this invention in this assay are described in Table II.

TABLE II

Plasma levels, duration, and in vivo potency of selected compounds of this invention.

|  | Example 1 | Example 2 | Example 3 |
|---|---|---|---|
| Rat Peritoneal Analphylaxis Model, oral ED$_{50}$ | 21.8 mg/Kg | 9.3 mg/Kg | 13.3 mg/Kg |
| Plasma Levels Rat, oral 200 μmol/Kg dose |  |  |  |
| ~1 hour | 126 μM | 259 μM | 109 μM |
| ~2 hours | 109 μM | 279 μM | 154 μM |
| ~4 hours | 129 μM | 245 μM | 178 μM |
| ~8 hours | 102 μM | 128 μM | 147 μM |
| Mouse, oral 100 mg/Kg dose |  |  |  |
| 1 hour |  | 257 μM |  |
| 2 hour |  | 205 μM |  |
| 4 hour |  | 92 μM |  |
| Plasma Duration |  |  |  |
| Rat, IV Half Life | 6 hours | 5.6 hours | 9.2 hours |
| Monkey, IV Half Life |  | 1.2 hours |  |
| Dog, IV Half Life |  | 1.4 hours |  |

|  | Example 4 | Example 5 | Example 6 |
|---|---|---|---|
| Plasma Levels Rat, oral 200 μmol/Kg dose |  |  |  |
| ~1 hour |  | 62 μM | 25 μM |
| ~2 hours |  | 129 μM | 39 μM |
| ~4 hours |  | 121 μM | 68 μM |
| ~8 hours |  | 92 μM | 78 μM |
| Plasma Duration |  |  |  |
| Rat, IV Half Life | 7.3 hours | 7.8 hours | 7.8 hours |
| Dog, IV Half Life |  |  | 2.5 hours |
| Monkey, IV Half Life |  |  | 1.3 hours |

While the foregoing examples are illustrative of compounds of the present invention, modifications will be apparent to those skilled in the art. Such modifications are to be considered within the scope of the present invention, unless the claims which follow expressly state otherwise.

What is claimed is:

1. Compounds of the formula:

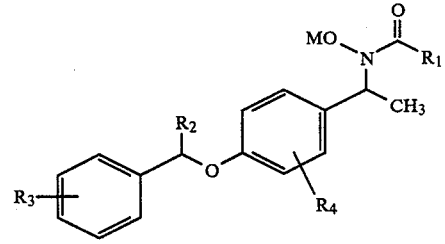

wherein $R_1$ is amino;
$R_2$ is $C_1$-$C_2$ alkyl;
$R_3$ and $R_4$ are hydrogen;
and M is hydrogen or a pharmaceutically acceptable cation.

2. A compound according to claim 1, wherein $R_2$ is methyl.

3. A compound of the formula:

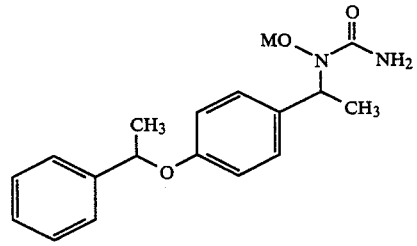

wherein M is hydrogen or a pharmaceutically acceptable cation.

4. A method of inhibiting 5- and/or 12-lipoxygenase activity in a mammal in need of such treatment, comprising administering to such mammal a therapeutically effective amount of a compound of the formula:

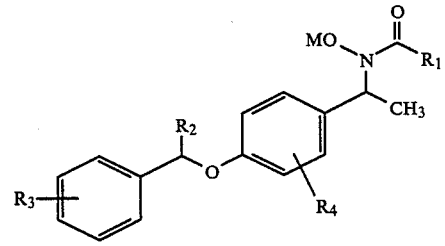

wherein $R_1$ is amino;
$R_2$ is $C_1$-$C_2$ alkyl;
$R_3$ and $R_4$ are hydrogen;
and M is hydrogen or a pharmaceutically acceptable cation.

5. The method according to claim 10, wherein $R_2$ is methyl.

6. A method of inhibiting 5- and/or 12-lipoxygenase activity in a mammal in need of such treatment, comprising administering to such mammal a therapeutically effective amount of a compound of the formula:

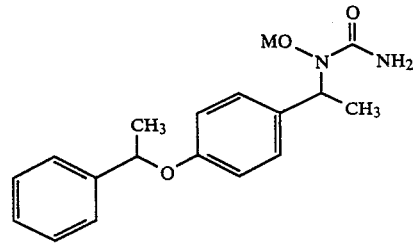

wherein M is hydrogen or a pharmaceutically acceptable cation.

* * * * *

UNITED STATES PATENT AND TRADEMARK OFFICE
CERTIFICATE OF CORRECTION

PATENT NO. : 4,897,422
DATED : January 30, 1990
INVENTOR(S) : James B. Summers, Jr.

It is certified that error appears in the above-identified patent and that said Letters Patent is hereby corrected as shown below:

Column 6, line 66: Replace "wherein" with --where--

Column 7, line 32, Replace "illustrates" with --illustrate--

Column 7, line 50, Replace "acetonphenone" with --acetophenone--

Column 9, line 34, Replace "(N+NH4)+," with --(M+NH4)+,--

Column 9, line 50, Replace "ethylydroxylamine" with --ethylhydroxylamine--

Column 10, line 21, Replace "$R_1=CH_3 R=C_2H_5$," with --$R_1=CH_3$, $R_2=C_2H_5$,--

Column 11, line 25, After "potassium" insert --salt--

Column 12, line 57, Replace "LTC" with --$LTC_4$--

Signed and Sealed this

Fifth Day of March, 1991

Attest:

HARRY F. MANBECK, JR.

Attesting Officer

Commissioner of Patents and Trademarks